United States Patent [19]

Nishiyama et al.

[11] 4,266,963
[45] May 12, 1981

[54] PYRAZOLE DERIVATIVES, HERBICIDAL COMPOSITIONS CONTAINING THE SAME, AND A PROCESS FOR THE PREPARATION OF THE SAME

[75] Inventors: Ryuzo Nishiyama, Takatsuki; Fumio Kimura, Kusatsu; Takahiro Haga, Kusatsu; Nobuyuki Sakashita, Kusatsu; Tetsuji Nishikawa, Kusatsu, all of Japan

[73] Assignee: Ishihara Sangyo Kaisha Ltd., Osaka, Japan

[21] Appl. No.: 128,060

[22] Filed: Mar. 7, 1980

[30] Foreign Application Priority Data

Mar. 7, 1979 [JP]  Japan ................................. 54-26564
Sep. 11, 1979 [JP]  Japan ................................. 54-116358

[51] Int. Cl.³ .................... A01N 43/56; C07D 231/20
[52] U.S. Cl. .......................................... 71/92; 548/377
[58] Field of Search ............................ 71/92; 548/377

[56] References Cited

U.S. PATENT DOCUMENTS 3,649,641  3/1972  Kim et al. ........................... 548/377
4,063,925  12/1977  Konotsune et al. ................... 71/92

FOREIGN PATENT DOCUMENTS 2002375  2/1979  United Kingdom ..................... 71/92

*Primary Examiner*—Glennon H. Hollrah
*Attorney, Agent, or Firm*—Sughrue, Rothwell, Mion, Zinn and Macpeak

[57] ABSTRACT

A pyrazole derivative having the formula (I):

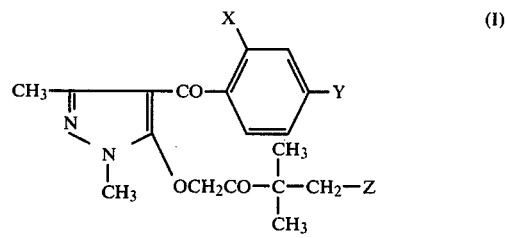

wherein X and Y each represents a chlorine atom, a nitro group or a trifluoromethyl group, and Z represents a hydrogen atom or a halogen atom, which is useful as a herbicidal component.

16 Claims, No Drawings

PYRAZOLE DERIVATIVES, HERBICIDAL COMPOSITIONS CONTAINING THE SAME, AND A PROCESS FOR THE PREPARATION OF THE SAME

BACKGROUND OF THE INVENTION

1. Field of the Invention

This invention relates to a novel compound useful as a herbicidal component, to a herbicidal composition containing the compound, and to a process for preparing the compound.

2. Description of the Prior Art

Recently, new types of herbicides which can effectively wither strong noxious weeds which more likely grow in the cultivated land at the initial to middle stages of a rice crop, such as annual weeds, e.g., barnyard grass (*Echinochloa crus-galli* Beauv.), toothcup (*Rotala indica* Koehne), bulrush (*Scirpus juncoides* var. Hotarui), chufa (*Cyperus microiria* Steud), etc., and perennial weeds, e.g., water plantain (*Sagittaria trifolia* L.), *Cyperus serotinus* Rottb., arrowhead (*Sagittaria pygmaea* Miq.), etc., have been demanded in the agricultural and horticultural fields.

In order to achieve these demands, herbicidal pyrazole compounds have already been proposed by, for example, U.S. Pat. No. 4,063,925 or British Patent Published Application No. 2,002,375.

The herbicidal pyrazole compounds according to the present invention are a compound having a novel chemical structure which has not hitherto been proposed, and these compounds exhibit a superior herbicidal activity against barnyard grass, bulrush, *Cyperus serotinus* Rottb. and the like as compared to the compounds disclosed in U.S. Pat. No. 4,063,925 or British Patent Published Application No. 2,002,375.

SUMMARY OF THE INVENTION

It is an object of the present invention to provide a novel herbicidal pyrazole derivative having the formula (I):

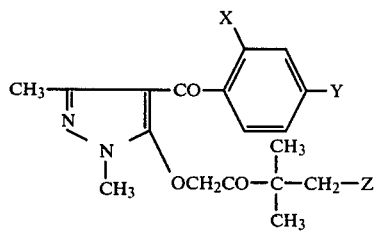

(I)

wherein X and Y each represents a chlorine atom, a nitro group or a trifluoromethyl group, and Z represents a hydrogen atom or a halogen atom.

It is another object of the present invention to provide a herbicidal composition comprising a herbicidally effective amount of at least one compound of the formula (I) as an active ingredient and agriculturally acceptable adjuvants.

It is a further object of the present invention to provide a process for preparing a novel pyrazole derivative of the formula (I).

DETAILED DESCRIPTION OF THE PREFERRED EMBODIMENTS

In the formula (I), suitable examples of the halogen atom for Z include a chlorine atom and a bromine atom.

Of the pyrazole derivatives expressed by the abovedescribed formula (I), compounds wherein both X and Y represent a chlorine atom are preferred from the standpoint of herbicidal activity with a compound wherein both X and Y represent a chlorine atom and Z represents a hydrogen atom or a chlorine atom being particularly preferred.

The pyrazole derivative of this invention of the formula (I) can be prepared by the following methods.

Method (A)

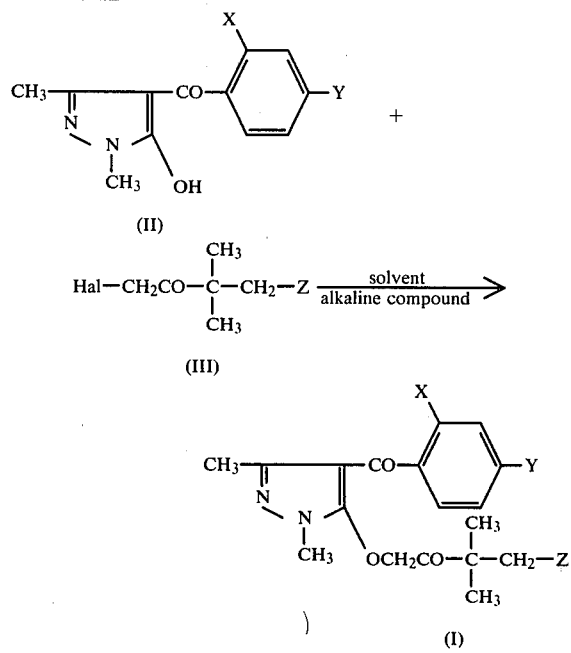

In the above reaction scheme, X, Y and Z are the same as defined hereinbefore, and Hal is a halogen atom such as a chlorine atom, a bromine atom, etc.

The above reaction is conducted at a temperature of from 50° to 170° C., preferably from 60° to 130° C. for from 1 to 10 hours in the presence of a solvent and an alkaline compound. Suitable examples of the solvent which can be used in the reaction include a ketone such as acetone, methyl ethyl ketone, methyl isobutyl ketone, etc., dimethylformamide, and an ether such as tetrahydrofuran, diisopropyl ether, dioxane, diethylene glycol dimethyl ether, etc. Suitable examples of the alkaline compound which can be used in the reaction include an alkali metal carbonate such as sodium carbonate and potassium carbonate, and an alkali metal hydroxide such as sodium hydroxide and potassium hydroxide.

In the above reaction, the presence of, as a catalyst, a cuprous halide such as cuprous iodide and cuprous fluoride will improve the reactivity of the reactants.

Method (B)

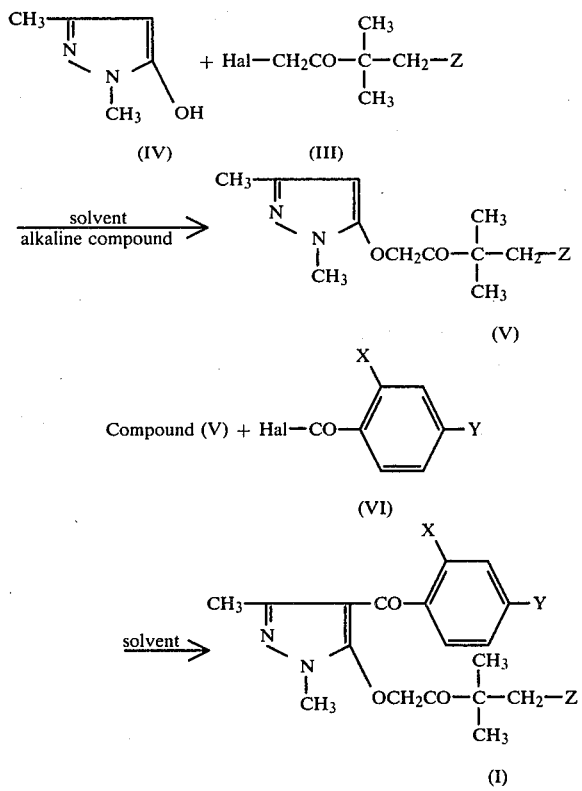

In the above reaction scheme, X, Y and Z are the same as defined hereinbefore, and Hal is a halogen atom such as a chlorine atom, a bromine atom, etc.

The above reaction of compound (IV) with compound (III) is conducted at a temperature of from 50° to 170° C., preferably from 60° to 130° C. for from 1 to 10 hours in the presence of a solvent and an alkaline compound.

The same materials as exemplified in method (A) above can also be used as the solvent and alkaline compound, respectively, in the reaction of compound (IV) with compound (III).

In the above reaction, the presence of, as a catalyst, a cuprous halide such as cuprous iodide and cuprous fluoride will improve the reactivity of the reactants.

The above reaction of compound (V) with compound (VI) is conducted at a temperature of from 0° to 100° C. for from 1 to 10 hours in the presence of a solvent. Suitable examples of the solvent which can be used in the reaction of compound (V) with compound (VI) include an ether such as diethyl ether, tetrahydrofuran, etc., and a halogenated hydrocarbon such as tetrachloroethane, etc.

In the reaction of compound (V) with compound (VI), the presence of, as a catalyst, a metal chloride such as aluminum chloride, zinc chloride, ferric chloride, etc. will effectively promote the reaction.

With respect to the starting materials used in methods (A) and (B) above, compound (II) is a known compound as disclosed in, for example, U.S. Pat. No. 4,063,925 or British Patent Published Application No. 2,002,375, and compounds (IV) and (VI) are a known compound as disclosed in, for example, U.S. Pat. No. 4,063,925. Furthermore, compound (III) is also a known compound as disclosed in, for example, British Pat. No. 1,533,175.

The following Preparation Examples are given to illustrate the preparation of some typical compounds of this invention, but they are not to be construed as limiting the present invention.

PREPARATION EXAMPLE 1

Preparation of 1,3-Dimethyl-4-(2,4-dichlorobenzoyl)-5-pivaloylmethoxypyrazole

Into a four necked flask was charged 0.45 g of 1,3-dimethyl-4-(2,4-dichlorobenzoyl)-5-hydroxypyrazole, and the contents were dissolved in 15 ml of methyl ethyl ketone. To the solution were added 0.5 g of anhydrous potassium carbonate and then 0.3 g of tert-butyl bromomethyl ketone while stirring, and the mixture was reacted for 2 hours under the reflux condition (80° C.). After completion of the reaction, the reaction product was collected by filtration, and the solvent (methyl ethyl ketone) was distilled off to obtain a crude product. The crude product was passed through a silica gel column (eluent: methylene chloride), and the eluent was distilled off to obtain 0.5 g of the titled compound having a melting point of 104° to 105° C.

PREPARATION EXAMPLE 2

Preparation of 1,3-Dimethyl-4-(2,4-dichlorobenzoyl)-5-(2,2-dimethyl-3-chloropropionylmethoxy)pyrazole Into a four necked flask was charged 1.0 g of 1,3-dimethyl-4-(2,4-dichlorobenzoyl)-5-hydroxypyrazole, and the contents were dissolved in 20 ml of methyl ethyl ketone. 0.54 g of anhydrous potassium carbonate was added thereto, and 0.75 g of 1,1-dimethyl-2-chloroethyl bromomethyl ketone was further dropwise added while stirring whereby the mixture was reacted for 2 hours under the reflux condition (80° C.). After completion of the reaction, the reaction product was collected by filtration, and the solvent (methyl ethyl ketone) was distilled off to obtain a crude product. The crude product was passed through a silica gel column (eluent: methylene chloride), and the eluent was distilled off to obtain 0.7 g of the titled compound having a melting point of 58° to 60° C.

Typical compounds prepared by the above methods are listed below. Reference by compound number designation set forth below will be made hereinafter in the specification.

Compound No. 1
1,3-Dimethyl-4-(2,4-dichlorobenzoyl)-5-pivaloylmethoxypyrazole
m.p. 104°–105° C.

Compound No. 2
1,3-Dimethyl-4-(2,4-dichlorobenzoyl)-5-(2,2-dimethyl-3-chloropropionylmethoxy)pyrazole
m.p. 58°–60° C.

Compound No. 3
1,3-Dimethyl-4-(2-chloro-4-trifluoromethylbenzoyl)-5-(2,2-dimethyl-3-chloropropionylmethoxy)pyrazole
m.p. 76°–77.5° C.

Compound No. 4
1,3-Dimethyl-4-(2-nitro-4-chlorobenzoyl)-5-(2,2-dimethyl-3-chloropropionylmethoxy)pyrazole
$n_D^{26}$ 1.5925

Compound No. 5

1,3-Dimethyl-4-(2,4-dichlorobenzoyl)-5-(2,2-dimethyl-3-bromopropionylmethoxy)pyrazole $n_D^{26}$ 1.6005

Herbicidal compositions containing of the pyrazole derivatives of this invention as active ingredients exhibit excellent herbicidal activities as shown in the Test Examples hereinafter described. In particular, at the initial to middle stages of a rice crop, the compounds of this invention will control noxious weeds such as barnyard grass, chufa, toothcup, bulrush, arrowhead, *Cyperus serotinus Rottb.* and the like without causing substantial phytotoxic activity on rice crop, so that these compositions are useful as herbicides for the paddy fields. Thus, by taking advantage of such herbicidal activities of the compounds, the herbicidal compositions of this invention can also be applied broadly to up-land fields, orchards, mulberry farms, forests, ridges, grounds, factory sites and the like in addition to the paddy fields by suitably selecting the application procedure, the amount of the composition to be used, etc. Also, such herbicidal compositions can be applied using various techniques such as soil treatment, foliar treatment and the like in a similar manner to conventional herbicidal compositions, as is well known in the art.

The pyrazole compound, as an active ingredient, of this invention can be dissolved directly or dispersed in water to produce an aqueous dispersion.

The compound of this invention can also be formulated into various forms such as an emulsifiable concentrate, a wettable powder, a water-miscible solution, a dust or granules by optionally incorporating conventional agriculturally acceptable adjuvants, for example, a solid carrier such as diatomaceous earth, slaked lime, calcium carbonate, talc, fine silicon dioxide, kaolin, bentonite or Jeeklite (trade name for kaolinite, produced by Jeeklite Co.), a solvent such as benzene, toluene, xylene, solvent naphtha, ethanol, dioxane, acetone, isophorone, methyl isobutyl ketone, dimethylformamide, dimethyl sulfoxide or water, or an anionic or nonionic surface active agent such as a sodium alkylsulfate, a sodium alkylbenzenesulfonate, sodium lignin sulfonate, polyoxyethylene lauryl ether, a polyoxyethylene alkylaryl ether, polyoxyethylene stylyl phenyl ether, a polyoxyethylene fatty acid ester, a polyoxyethylene sorbitan fatty acid ester, a sodium naphthalene sulfonateformaldehyde condensate, a sulfate of a polyoxyethylene alkylaryl ether, polyethyleneglycol oleyl ether or polyethyleneglycol dodecylphenyl ether.

Suitable amounts of these components are 1 to 90% by weight, preferably 1 to 70% by weight for the active ingredient, 5 to 99% by weight, preferably 25 to 99% by weight for the solid carrier or solvent, and 0 to 30% by weight, preferably 1 to 20% by weight for the surface active agent, respectively.

The herbicidal composition of this invention can also be mixed or used together with suitable agricultural chemicals such as other herbicides, insecticides or fungicides, or mixed with an agricultural agent such as a fertilizer or soil conditioner or soil or sand, at the time of formulation or application. Sometimes, such joint usage brings about improved effects.

A suitable rate of application varies according to various factors such as the climatic conditions, the soil conditions, the form of the chemical, the time of application, the method of application, or the types of cultivated crops to which it is applied and the main weeds to be controlled. Usually the amount of the active ingredient is 1 to 500 g per are (100 m$^2$), preferably 10 to 100 g per are.

The Test Examples and Formulation Examples of the herbicidal compositions of this invention are described below. This invention is, however, not construed to be limited thereto.

TEST EXAMPLE 1

Each 1/5,000 are (1/50 m$^2$) pot was charged with paddy soil and saturated with water. Predetermined amounts of seeds of edible barnyard grass were sown and lightly covered with soil. The edible barnyard grass was germinated under the upland farm conditions and then grown under the flooded conditions of a depth of water of about 3 cm. After coleoptiles appeared, the edible barnyard grass was subjected to dropwise treatment with a predetermined amount of an aqueous dispersion of each of the compounds shown in Table 1 below, and the growth of the edible barnyard grass was visually evaluated three weeks after the treatment. The results obtained are shown in Table 1. The degree of growth inhibition shown in Table 1 was evaluated in accordance with the following standard (scale of 5 grades).

TABLE 1

5: complete withering
4: about 80% withering
3: about 50% withering
2: about 20% withering
1: no growth inhibiton

| Test Compound | Degree of Growth Inhibition Amount of Active Ingredient (g/are) | | | |
|---|---|---|---|---|
| | 30 | 15 | 15/2 | 15/4 |
| Compound No. 1 | 5 | 5 | 5 | 5 |
| Compound No. 2 | 5 | 5 | 5 | 5 |
| Compound No. 3 | 5 | 5 | 5 | 5 |
| Compound No. 4 | 5 | 5 | 4 | 4 |
| Compound No. 5 | 5 | 5 | 5 | 5 |
| 1,3-Dimethyl-4-(2,4-dichlorobenzoyl)-5-acetylmethoxypyrazole* | 5 | 1 | 1 | 1 |

*compound according to British Patent Published Application No. 2,002,375

TEST EXAMPLE 2

Each 1/5,000 are (1/50 m$^2$) pot was charged with soil to provide flooded conditions. Predetermined amounts of seeds of bulrush were sown and at the same time, tubers of arrowhead were planted, and both plants were grown in a green house. When the bulrush and arrowhead reached an about one-leaf stage, the depth of water was set up about 3 cm, and the test plants were subjected to dropwise treatment with a predetermined amount of an aqueous dispersion of each of the compounds shown in Table 2 below. Three weeks after the treatment, the growth of the test plants was visually evaluated, and the degree of growth inhibition was evaluated on the same scale as in Test Example 1. The results obtained are also shown in Table 2 below.

TABLE 2

| Test Compound | Amount Active Ingredient (g/are) | Degree of Growth Inhibition | |
|---|---|---|---|
| | | Bulrush | Arrowhead |
| Compound No. 1 | 30 | 5 | 5 |
| | 15 | 5 | 5 |
| | 15/2 | 5 | 4 |
| Compound No. 2 | 30 | 5 | 5 |
| | 15 | 5 | 5 |
| | 15/2 | 5 | 4 |

TABLE 2-continued

| Test Compound | Amount Active Ingredient (g/are) | Degree of Growth Inhibition | |
|---|---|---|---|
| | | Bulrush | Arrowhead |
| | 30 | 5 | 5 |
| Compound No. 3 | 15 | 5 | 5 |
| | 15/2 | 5 | 5 |
| | 30 | 5 | 5 |
| Compound No. 4 | 15 | 5 | 5 |
| | 15/2 | 5 | 4 |
| | 30 | 5 | 5 |
| Compound No. 5 | 15 | 5 | 5 |
| | 15/2 | 5 | 4 |
| 1,3-Dimethyl-4-(3- | 30 | 2 | 2 |
| nitrobenzoyl)-5- | 15 | 1 | 1 |
| hydroxypyrazole* | 15/2 | 1 | 1 |

*compound according to U.S. Pat. No. 4,063,925

TEST EXAMPLE 3

Each 1/5,000 are (1/50 m²) pot was charged with paddy soil and saturated with water. Tubers of Cyperus serotinus Rottb. were planted therein. The test plant was germinated under the upland farm conditions and then grown under the flooded conditions of a depth of water of about 3 cm. When the plant reached an about 0.5-leaf stage, the plant was subjected to dropwise treatment with a predetermined amount of an aqueous dispersion of each of the compounds shown in Table 3 below. Three weeks after the treatment, the growth of the test plant was visually evaluated, and the degree of growth inhibition was evaluated on the same scale as in Test Example 1. The results obtained are also shown in Table 3 below.

TABLE 3

| Test Compound | Degree of growth Inhibition Amount of Active Ingredient (g/are) | | |
|---|---|---|---|
| | 30 | 15 | 15/2 |
| Compound No. 1 | 5 | 5 | 5-4 |
| Compound No. 2 | 5 | 5-4 | 4 |
| Compound No. 3 | 5 | 5 | 5-4 |
| Compound No. 4 | 5 | 4 | 4 |
| Compound No. 5 | 5 | 5-4 | 4 |

FORMULATION EXAMPLE 1

| (1) Bentonite | 58 wt. parts |
|---|---|
| (2) Jeeklite | 30 wt. parts |
| (3) Sodium Lignin Sulfonate | 5 wt. parts |

Components (1) to (3) were mixed and granulated. A solution prepared by diluting 7 wt. parts of 1,3-dimethyl-4-(2,4-dichlorobenzoyl)-5-pivaloylmethoxypyrazole with a suitable amount of acetone was sprayed on the granulated components to form granules.

FORMULATION EXAMPLE 2

| (1) Jeeklite | 78 wt. parts |
|---|---|
| (2) Sodium Naphthalene Sulfonate-Formaldehyde Condensate | 2 wt. parts |
| (3) Sulfate of Polyoxyethylene Alkylaryl Ether | 5 wt. parts |
| (4) Fine Silicon Dioxide ($SiO_2 \cdot nH_2O$) | 15 wt. parts |

Components (1) to (4) were mixed and the mixture obtained was then mixed with 1,3-dimethyl-4-(2,4-dichlorobenzoyl)-5-(2,2-dimethyl-3-chloropropionyl- methoxy)pyrazole in a ratio of 4:1 by weight to form a wettable powder.

FORMULATION EXAMPLE 3

| (1) 1,3-Dimethyl-4-(2,4-dichlorobenzoyl)-5-(2,2-dimethyl-3-bromopropionylmethoxy)-pyrazole | 20 wt. parts |
|---|---|
| (2) Xylene | 60 wt. parts |
| (3) Polyoxyethylene Stearate | 20 wt. parts |

Components (1) to (3) were uniformly mixed to form an emulsifiable concentrate.

While the invention has been described in detail and with reference to specific embodiments thereof, it will be apparent to one skilled in the art that various changes and modifications can be made therein without departing from the spirit and scope thereof.

What is claimed is:

1. A pyrazole derivative having the formula (I):

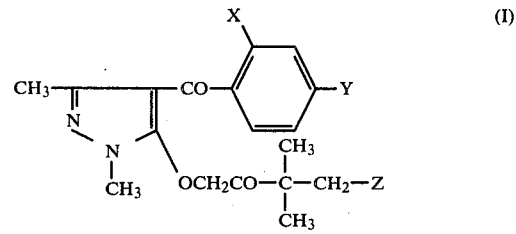

wherein X and Y each represents a chlorine atom, a nitro group or a trifluoromethyl group, and Z represents a hydrogen atom or a halogen atom.

2. The pyrazole derivative according to claim 1, wherein X represents a chlorine atom or a nitro group, and Y represents a chlorine atom or a trifluoromethyl group.

3. The pyrazole derivative according to claim 1, wherein X and Y each represents a chlorine atom.

4. The pyrazole derivative according to claim 1, wherein X and Y each represents a chlorine atom, and Z represents a hydrogen atom, a chlorine atom or a bromine atom.

5. The pyrazole derivative according to claim 1, wherein X and Y each represents a chlorine atom, and Z represents a hydrogen atom or a chlorine atom.

6. 1,3-Dimethyl-4-(2,4-dichlorobenzoyl)-5-pivaloylmethoxypyrazole.

7. 1,3-Dimethyl-4-(2,4-dichlorobenzoyl)-5-(2,2-dimethyl-3-chloropropionylmethoxy)pyrazole.

8. 1,3-Dimethyl-4-(2,4-dichlorobenzoyl)-5-(2,2-dimethyl-3-bromopropionylmethoxy)pyrazole.

9. A herbicidal composition comprising a herbicidally effective amount of at least one compound having the formula (I):

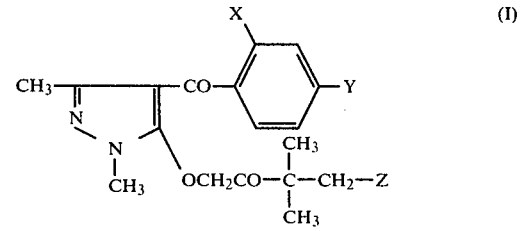

wherein X and Y each represents a chlorine atom, a nitro group or a trifluoromethyl group, and Z represents a hydrogen atom or a halogen atom as an active ingredient, and agriculturally acceptable adjuvants not deleteriously affecting desired plants.

10. The herbicidal composition according to claim 9, wherein X represents a chlorine atom or a nitro group, and Y represents a chlorine atom or a trifluoromethyl group.

11. The herbicidal composition according to claim 9, wherein X and Y each represents a chlorine atom.

12. The herbicidal composition according to claim 9, wherein X and Y each represents a chlorine atom, and Z represents a hydrogen atom, a chlorine atom or a bromine atom.

13. The herbicidal composition according to claim 9, wherein X and Y each represents a chlorine atom, and Z represents a hydrogen atom or a chlorine atom.

14. The herbicidal composition according to claim 9, wherein the active ingredient is 1,3-dimethyl-4-(2,4-dichlorobenzoyl)-5-pivaloylmethoxypyrazole.

15. The herbicidal composition according to claim 9, wherein the active ingredient is 1,3-dimethyl-4-(2,4-dichlorobenzoyl)-5-(2,2-dimethyl-3-chloropropionylmethoxy)pyrazole.

16. The herbicidal composition according to claim 9, wherein the active ingredient is 1,3-dimethyl-4-(2,4-dichlorobenzoyl)-5-(2,2-dimethyl-3-bromopropionylmethoxy)pyrazole.

* * * * *